United States Patent
Hsiao et al.

(10) Patent No.: US 9,834,561 B2
(45) Date of Patent: Dec. 5, 2017

(54) PROCESS FOR PREPARING IBRUTINIB AND ITS INTERMEDIATES

(71) Applicant: SCINOPHARM TAIWAN, LTD., Tainan (TW)

(72) Inventors: Tsung-Yu Hsiao, Tainan (TW); MengFen Ho, Tainan (TW); HsinChang Tseng, Tainan (TW); WenShing Tsao, Tainan (TW); YuanChang Huang, Tainan (TW); Wei-Shuo Lo, Tainan (TW)

(73) Assignee: SCINOPHARM TAIWAN, LTD., Tainan (TW)

( * ) Notice: Subject to any disclaimer, the term of this patent is extended or adjusted under 35 U.S.C. 154(b) by 0 days.

(21) Appl. No.: 15/336,418

(22) Filed: Oct. 27, 2016

(65) Prior Publication Data

US 2017/0145017 A1 May 25, 2017

Related U.S. Application Data

(60) Provisional application No. 62/285,035, filed on Oct. 28, 2015.

(51) Int. Cl.

| | |
|---|---|
| *A01N 43/90* | (2006.01) |
| *A61K 31/519* | (2006.01) |
| *C07D 487/00* | (2006.01) |
| *C07D 487/04* | (2006.01) |
| *C07F 9/6561* | (2006.01) |
| *C07D 401/04* | (2006.01) |

(52) U.S. Cl.
CPC .......... *C07D 487/04* (2013.01); *A61K 31/519* (2013.01); *C07D 401/04* (2013.01); *C07F 9/6561* (2013.01)

(58) Field of Classification Search
CPC .................................................. A61K 31/519
USPC ........................................ 514/262.1; 544/262
See application file for complete search history.

(56) References Cited

U.S. PATENT DOCUMENTS

| | | |
|---|---|---|
| 8,158,786 B2 | 4/2012 | Honigberg et al. |
| 2014/0275126 A1 | 9/2014 | Pye et al. |
| 2016/0264584 A1 | 9/2016 | Xu |

FOREIGN PATENT DOCUMENTS

| | | |
|---|---|---|
| CN | 103121999 A | 5/2013 |
| CN | 104557945 A | 4/2015 |
| WO | WO-2015/074464 A1 | 5/2015 |
| WO | WO-2015/145415 A2 | 10/2015 |
| WO | WO-2015/145415 A3 | 10/2015 |
| WO | WO-2016/115869 A1 | 7/2016 |

OTHER PUBLICATIONS

International Search Report dated Feb. 6, 2017, for PCT Application No. PCT/SG2016/050528, filed Oct. 28, 2016, 4 pages.
Liu, N. et al. (May 14, 2015). "Direct and two-step bioorthogonal probes for Bruton's tyrosine kinase based on ibrutinib: a comparative study," *Org Biomol Chem* 13(18):5147-5157.
Written Opinion dated Feb. 6, 2017, for PCT Application No. PCT/SG2016/050528, filed Oct. 28, 2016, 13 pages.

*Primary Examiner* — Jeffrey H Murray
(74) *Attorney, Agent, or Firm* — Mintz Levin Cohn Ferris Glovsky and Popeo, P.C.

(57) ABSTRACT

The present invention provides efficient, economical, and improved methods for synthesizing ibrutinib and intermediates thereof. The invention involves a unique biphasic acylation reaction system which advantageously allows for easy separation of ibrutinib from the reaction mixture without additional extraction and wash steps. The isolated ibrutinib formed using the methods described herein can be useful in the preparation of an amorphous form of ibrutinib. In some embodiments, the isolated ibrutinib produced by the processes described herein is a homogenous solution of ibrutinib and DMSO which may be directly used in the formation of the amorphous polymorph. In some embodiments, the isolated ibrutinib is solid ibrutinib. The solid ibrutinib may also be used in the formation of amorphous ibrutinib.

30 Claims, 2 Drawing Sheets

Figure 1

Scheme 3

Figure 2

An X-ray powder diffraction pattern for of an amorphous form of ibrutinib characterized by X-ray powder diffractometer with a broad peak.

PROCESS FOR PREPARING IBRUTINIB AND ITS INTERMEDIATES

CROSS-REFERENCES TO RELATED APPLICATIONS

This application claims the benefit of priority under 35 U.S.C. §119(e) to U.S. Provisional Application No. 62/285,035, filed on Oct. 28, 2015 entitled PROCESS FOR PREPARING IBRUTINIB AND ITS INTERMEDIATES, the disclosure of which is incorporated herein by reference in its entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Ibrutinib is an oral Bruton's tyrosine kinase (BTK) inhibitor for the treatment of mantle cell lymphoma, chronic lymphocytic leukemia, and Waldenström's macroglobulinemia. The chemical name of Ibrutinib is 1-[(3R)-3-[4-amino-3-(4-phenoxyphenyl)-1H-pyrazolo[3,4-d]pyrimidin-1-yl]-1-piperidinyl]-2-propen-1-one. The structure of ibrutinib is shown below.

Synthesis of ibrutinib and intermediates thereof has been disclosed in U.S. Pat. No. 8,158,786, Honigberg et al., shown below as Scheme 1.

Scheme 1-The process for preparing ibrutinib as disclosed in U.S. Patent No. 8,158,786 B2

Ibrutinib

Honigberg et al. disclose a process for preparing ibrutinib by coupling compound 9 with compound 10 under Mitsunobu reaction conditions to obtain compound 7a, deprotecting compound 7a (i.e. removal of the Boc group) to form compound 8a, and acylating the nitrogen of the 3-piperidine moiety of compound 8a with acryloyl chloride using standard acylation conditions to form ibrutinib. According to this process, compound 9 is coupled with compound 10 in the presence of polymer-bound triphenylphosphine (TPP), and ibrutinib is formed by acylating compound 8a using organic solvent (dichloromethane, DCM) and organic base (triethylamine, $NEt_3$). In order to isolate ibrutinib from the acylation reaction mixture, multiple extraction and wash steps are required.

U.S. Patent Publication No. 2014/0275126 A1, Pye et al., discloses a similar process for preparing ibrutinib shown in Scheme 2, below.

Scheme 2- The process for preparing ibrutinib as disclosed in US 2014/0275126 A1

6a: $R_1$ = Boc
6b: $R_1$ = Bn
6c: $R_1$ = Cbz formamide acetate

In this reaction scheme, compound 6 is formed by reacting compound 4, which is derived from a series of prior reactions, with a hydrazine derivative. The pyrimidine portion of compound 7 is prepared by reacting compound 6 with formamide. Similar to the disclosure of Honigberg et al., compound 8 is prepared by deprotecting compound 7, and ibrutinib is obtained by acylating the nitrogen of the 3-piperidine moiety of compound 8 with acryloyl chloride using standard acylation conditions to form ibrutinib. As in Honigberg et al., the isolation of ibrutinib from the acylation reaction mixture requires multiple extraction and wash steps.

In view of the foregoing, the need exists for an improved process to produce ibrutinib with commercially acceptable yields and increased efficiency.

BRIEF SUMMARY OF THE INVENTION

In one aspect, the present invention provides processes useful for the preparation of ibrutinib.

In one embodiment, the process includes:

(1) combining (S)-3-hydroxypiperidine hydrochloride with trifluoroacetic anhydride to form compound 11

(2) contacting compound 11 with compound 9 to form a reaction mixture;

(3) subjecting the reaction mixture to Mitsunobu reaction conditions to obtain compounds 12 and 12a and

(4) deprotecting compounds 12 and 12a to form compound 8

(5) combining compound 8 with acryloyl chloride in the presence of inorganic base to form an acylation reaction mixture; and (6) isolating ibrutinib from said acylation reaction mixture to afford isolated ibrutinib.

In another aspect, the invention provides novel compounds including those according to structures 12 and 12a.

In another aspect, the present invention provides processes for the preparation of an amorphous form of ibrutinib.

In some embodiments, the process for preparing the amorphous form of ibrutinib includes:

(a) dissolving ibrutinib in dimethyl sulfoxide to achieve a homogeneous solution; and

(b) contacting the homogeneous solution from step (a) with water to obtain amorphous ibrutinib.

In some embodiments, the process for preparing the amorphous form of ibrutinib includes:

(1) combining (S)-3-hydroxypiperidine hydrochloride with trifluoroacetic anhydride to form compound 11

(2) contacting compound 11 with compound 9 to form a reaction mixture;

(3) subjecting the reaction mixture to Mitsunobu reaction conditions to obtain compounds 12 and 12a (4) deprotecting compounds 12 and 12a to form compound 8

(5) combining compound 8 with acryloyl chloride in the presence of inorganic base to form an acylation reaction mixture;

(6) isolating ibrutinib from said acylation reaction mixture to afford isolated ibrutinib, wherein the isolated ibrutinib comprises an ibrutinib/DMSO solution; and (7) contacting the ibrutinib/DMSO solution with water to obtain amorphous ibrutinib.

DETAILED DESCRIPTION OF THE INVENTION

I. General

The present invention provides improved processes for the preparation of ibrutinib and intermediates thereof. Specifically, an acylation reaction of compound 8 with acryoyl chloride in the presence of inorganic base has been discovered. The process provides a biphasic reaction system in the acylation reaction which allows for easy separation of the two phases after completion of the reaction in a single extraction. This avoids multiple, repeating extraction and wash steps required in conventional methods. Accordingly, the present invention is time-saving and suitable for industrial manufacturing. Also provided herein are novel processes for preparing an amorphous form of ibrutinib.

Figure 1:
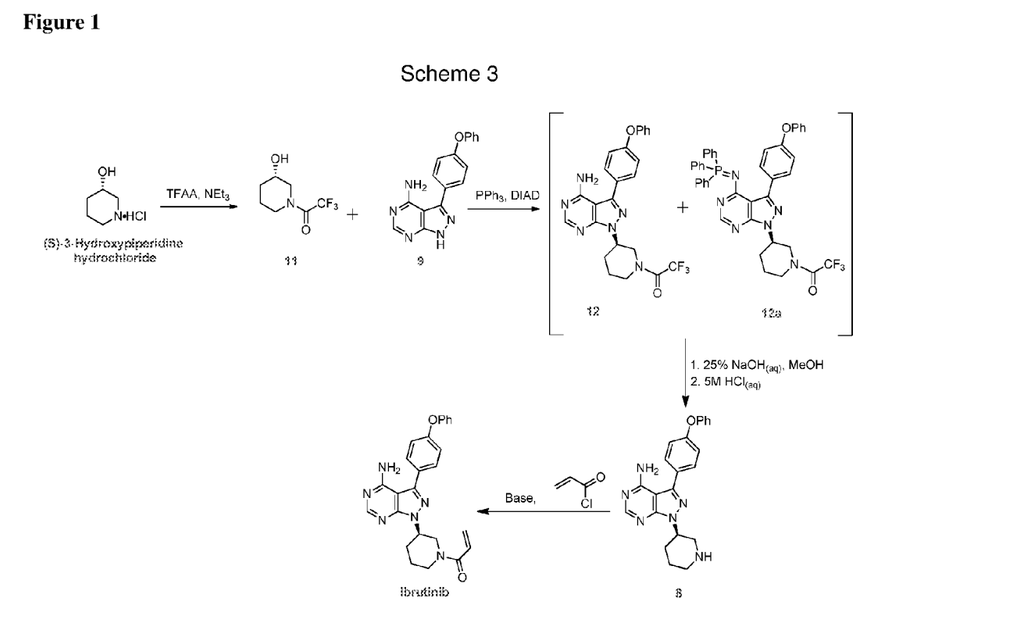
FIG. 1 provides a scheme as provided herein for the preparation of ibrutinib.

While a complete synthetic scheme is provided in the summary of the invention, as well as Scheme 3 (FIG. 1), one of skill in the art will appreciate that selected steps of the instant processes are novel and can be performed independent of the origin of the starting material or intermediates.

II. Definitions

As used herein, the term "contacting" refers to the process of bringing into contact at least two distinct species such that they can react. It should be appreciated, however, that the resulting reaction product can be produced directly from a reaction between the added reagents or from an intermediate from one or more of the added reagents which can be produced in the reaction mixture.

As used herein, the term "alkyl" by itself or as part of another substituent, means, unless otherwise stated, a straight or branched chain hydrocarbon radical. Alkyl substituents, as well as other hydrocarbon substituents, may contain number designators indicating the number of carbon atoms in the substituent (i.e. $C_1$-$C_8$ means one to eight carbons), although such designators may be omitted. Unless otherwise specified, the alkyl groups of the present invention contain 1 to 12 carbon atoms. For example, an alkyl group can contain 1-2, 1-3, 1-4, 1-5, 1-6, 1-7, 1-8, 1-9, 1-10, 1-11, 1-12, 2-3, 2-4, 2-5, 2-6, 3-4, 3-5, 3-6, 4-5, 4-6 or 5-6 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like.

As used herein, the term "alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more.

As used herein, the term "acyl" refers to an alkyl or alkenyl radical as described above, wherein the carbon atom attached to the remainder of a molecule is substituted with an oxo group so as to form a C=O bond. Examples of acyl groups include, but are not limited to, acetyl, propionyl, butyryl.

As used herein, the term "protecting group" refers to a moiety that is formed to render a functional moiety unreactive. The protecting group can be removed so as to restore the functional moiety to its original state. Various protecting groups and protecting reagents, including nitrogen protecting groups, are well known to one of ordinary skill in the art and include compounds that are disclosed in *Protective Groups in Organic Synthesis,* 4th edition, T. W. Greene and P. G. M. Wuts, John Wiley & Sons, New York, 2006, which is incorporated herein by reference in its entirety.

As used herein, the term "biphasic reaction system" refers to a reaction system having two phases. An example of a biphasic reaction system is one containing an aqueous phase and an organic phase.

As used herein, the term "basic" is an adjective that refers to a chemical substance that is a base. A basic additive refers to an additive that is a base. A basic reaction condition refers to a reaction condition that includes a pH value above 7.

III. Embodiments of the Invention

In one embodiment, provided herein is a process for preparing ibrutinib, comprising:

(1) combining (S)-3-hydroxypiperidine hydrochloride with trifluoroacetic anhydride to form compound 11

11

(2) contacting compound 11 with compound 9

9 to form a reaction mixture;

(3) subjecting the reaction mixture to Mitsunobu reaction conditions to obtain compounds 12 and 12a

12

12a and (4) deprotecting compounds 12 and 12a to form compound 8

8

(5) combining compound 8 with acryloyl chloride in the presence of inorganic base to form an acylation reaction mixture; and (6) isolating ibrutinib from said acylation reaction mixture.

As noted in the summary of the invention, a person of skill in the art will appreciate that selected steps in the process may be conducted independent of the origin of starting material or intermediates.

For example, in one embodiment, step (5) can be conducted independent of the process used to prepare compound 8. In this embodiment, ibrutinib is prepared by (5) combining compound 8

8 with acryloyl chloride in the presence of inorganic base to form an acylation reaction mixture; and
(6) isolating ibrutinib from said acylation reaction mixture.

The acylation of compound 8 can be achieved using a variety of inorganic bases. The inorganic base can be, but is not limited to, $Li_2CO_3$, $K_2CO_3$, $Cs_2CO_3$, $Na_2CO_3$, $NaHCO_3$, and $KHCO_3$. In some embodiments, the inorganic base is selected from $Li_2CO_3$, $K_2CO_3$, $Cs_2CO_3$, $Na_2CO_3$, $NaHCO_3$, $KHCO_3$, and combinations thereof.

In some embodiments, the acylation of compound 8 is conducted in an aqueous solvent mixture comprising one or more organic solvents. A person or ordinary skill in the art will recognize that the order of addition of compounds and solvents is not required in successfully converting compound 8 to ibrutinib. In some embodiments, the aqueous solvent mixture is a biphasic reaction system comprising an aqueous phase and an organic phase. In some embodiments, compound 8 is dissolved in water, inorganic base and organic solvent. In some embodiments, acryloyl chloride dissolved in organic solvent is added to compound 8 dissolved in water, inorganic base, and organic solvent. In some embodiments acryloyl chloride is slowly added. Slow addition can include continuous addition of the reagent to the reaction mixture at a rate of about 1.2 mL/minute, about 0.82 mL/minute, about 0.62 mL/minute, about 0.41 mL/minute, about 0.31 mL/minute, about 0.25 mL/minute, or about 0.21 mL/minute. In some embodiments, the acylation reaction mixture further comprises butylated hydroxytoluene.

The acylation of compound 8 can be carried out in one or more organic solvents. The one or more organic solvents can be, but is not limited to, dichloromethane, ethyl acetate, 2-methyltetrahydrofuran, isopropyl acetate, and combinations thereof. In some embodiments, the one or more organic solvents are selected from dichloromethane, 2-methyltetrahydrofuran or combinations thereof. In some embodiments, the one or more organic solvents is dichloromethane.

After the acylation of compound 8 is complete, isolation of ibrutinib can be achieved by removal of the aqueous phase. In some embodiments, ibrutinib is isolated in step (6) by removal of the aqueous phase without washing steps. The remaining organic layer including ibrutinib can be optionally concentrated under reduced pressure by any known means in the art, and optionally purified by column chromatography using any known means in the art. In some embodiments, ibrutinib is purified using silica gel column chromatography with a mobile phase. In some embodiments, the mobile phase is a MeOH/DCM mixture (3:97). In some embodiments the mobile phase is an EtOAc/Acetone mixture.

In some embodiments, isolation of ibrutinib in step (6) is achieved by (i-a) removing the aqueous phase and (ii-a) concentrating the organic phase to afford solid isolated ibrutinib. In some embodiments, the organic phase is removed via the concentrating step such that only solid amorphous ibrutinib remains. In some embodiments, isolation of ibrutinib is achieved by (i-b) removing the aqueous phase, (ii-b) concentrating the organic phase, and (iii-b) adding DMSO to afford an isolated ibrutinib/DMSO solution. It is understood from the present disclosure that the addition of DMSO may be made before, during, and/or after the concentration of the organic phase in step (ii-b). In some embodiments, DMSO is an organic solvent used in the conversion of step (5). In such embodiments, additional DMSO is optionally added. In particular embodiments, DMSO is added after an initial concentration of the organic phase.

In some embodiments, the ibrutinib/DMSO solution formed in step 6 is substantially free of another solvent. In some embodiments, substantially free refers to 5% or less, 4% or less, 3% or less, 2% or less, 1% or less, or 0.5% or less of an additional organic solvent (v/v).

In some embodiments, column chromatography is optionally included prior to step (ii-a) or (ii-b) in either of the above described embodiments.

The acylation of compound 8 in step (5) can be conducted at various temperatures. In some embodiments, the acylation of compound 8 in step (5) is conducted at a temperature below 40° C. In some embodiments, the acylation of compound 8 in step (5) is conducted at a temperature of about 20-30° C.

In a selected group of embodiments, the process utilizes compound 8, which can be prepared by (2) contacting compound 11

11 with compound 9

9 to form a reaction mixture;
(3) subjecting the reaction mixture to Mitsunobu reaction conditions to obtain compounds 12 and 12a and
(4) deprotecting compounds 12 and 12a.

A Mitsunobu reaction is a well-known chemical transformation that was first reported in 1967 (Mitsunobu et al. *Bull. Chem. Soc. Jpn.*, 40 (10): 2380-2382 (1967)). One of skill in the art will recognize that the Mitsunobu reaction conditions of step (3) include an inert atmosphere, triphenylphosphine, a solvent, and an azodicarboxylate. The azodicarboxylate can include, but not limited to, diethyl azodicarboxylated or diisopropyl azodicarboxylated. In some embodiments, the Mitsunobu reaction conditions of step (3) include an inert atmosphere, triphenylphosphine, a solvent, and dissopropyl azodicarboxylate. The inert atmosphere can include any suitable inert gas including nitrogen, argon, neon and combinations thereof. In some embodiments, the inert atmosphere is nitrogen. The solvent can include any suitable solvent including tetrahydrofuran, 2-methyltetrahydrofuran, dimethylformamide, dichlormethane, and combinations thereof. In some embodiments, the solvent is tetrahydrofuran.

The Mitsunobu reaction of step (3) can be conducted by adding diisopropyl azodicarboxylate to a mixture of compound 11 and compound 9, but addition of particular solvents or compounds is not required to successfully perform this chemical conversion. In some embodiments, a mixture of compound 11 and compound 9 are dissolved in an organic solvent under an inert atmosphere and an azodicarboxylate dissolved in an organic solvent is added to the mixture of compound 11 and compound 9. In some embodiments, the azodicarboxylate is slowly added to the reaction mixture. Slow addition can include continuous addition of the reagent to the reaction mixture at a rate of about 3.0 mL/minute, about 2.7 mL/minute, about 1.8 mL/minute, about 1.3 mL/minute, 0.88 mL/minute, or about 0.66 mL/minute.

The Mitsunobu reaction in step (3) can be conducted at various temperatures. In some embodiments, the Mitsunobu reaction in step (3) is conducted at a temperature of about 20-30° C.

The deprotection step in step (4) to remove the protecting group from the nitrogen of the 3-piperidineyl moiety of compounds 12 and 12a and the triphenylphosphoranimine group from the exocyclic amine of the pyrimidine moiety of compound 12a can be performed by any known means in the art. For example, compounds 12 and 12a can be deprotected in two successive steps. First, compounds 12 and 12a are combined with a strong base and an organic solvent to form a basic deprotection reaction mixture. After completion of the basic deprotection reaction, a strong acid is added to form an acidic deprotection reaction mixture. In some embodiments, the deprotection step in step (4) includes (i) combining compounds 12 and 12a with sodium hydroxide (NaOH) and methanol (MeOH) to form a basic deprotection reaction mixture; and (ii) adding a sufficient amount of hydrogen chloride (HCl) to the basic deprotection reaction mixture to form an acidic deprotection reaction mixture. Generally, a sufficient amount of HCl has been added to the acidic deprotection reaction mixture when the pH of the acidic deprotection reaction mixture ranges from below 0 to about 6.

In some embodiments, the pH of the deprotection reaction mixture ranges from about −2 to about 2, from about 0 to about 2, from about 2 to about 4, from about 0 to 4, or from about 4 to about 6.

The basic deprotection reaction mixture can range in pH from about 8 to above 14. In some embodiments, the pH of the basic deprotection reaction mixture ranges from about 13 to about 16, from about 12 to about 14, from about 10 to about 12, from about 10 to about 14, or from about 8 to about 11. In some embodiments, step (4)(i) is conducted at about 20-30° C. In some embodiments, step (4)(ii) is conducted at about 40-55° C.

Further extraction and purification of compound 8 can be performed using any known means in the art including liquid-liquid extraction, column chromatography, and crystallization. In some embodiments, after the second deprotection reaction, liquid-liquid extraction is performed with the addition of water and an organic solvent, and compound 8 is isolated by adding a base to the extracted aqueous solvent to precipitate compound 8. The precipitated compound 8 can then be filtered and dried to remove solvent. In some embodiments, ethyl acetate (EtOAc) is the organic solvent used in the extraction. In some embodiments, NaOH is used to precipitate compound 8.

The Mitsunobu reaction creating compound 8 utilizes compound 11, which in some embodiments can be prepared by
(1) combining (S)-3-hydroxypiperidine hydrochloride with trifluoroacetic anhydride to form compound 11.

The acylation of compound 11 can be achieved using a variety of organic solvents. The organic solvent can be, but is not limited to, dichloromethane, dimethylformamide, 2-methyltetrahydrofuran or combinations thereof. In some embodiments, the organic solvent is dichloromethane. In some embodiments, the preparation of compound 8 further comprises triethylamine. A person of skill in the art will recognize that the order of adding reaction components or the particular solvent used is not critical in the formation of compound 11. In some embodiments an alternative protecting group is used instead of trifluoroacetic acid. The protecting group can be any useful nitrogen protecting group known in the art.

Further extraction and purification of compound 11 can be performed using any known means in the art including liquid-liquid extraction and column chromatography. For example, after the reaction is complete the reaction can be quenched by addition of acid, followed by liquid-liquid extraction, concentration, and column chromatography. In some embodiments, the reaction is quenched with addition of 1M HCl. In some embodiments, the aqueous phase is removed during liquid-liquid extraction. In some embodiments, the remaining organic layer after liquid-liquid extraction is concentrated and purified on a silica gel column using a mixture of organic solvents as the mobile phase. In some embodiments, the mobile phase is a n-heptane/EtOAc mixture (4:1).

In a related aspect, the present invention provides novel compounds including those according to structures 12 and 12a.

In another aspect, the present invention provides a process for the preparation of an amorphous form of ibrutinib.

In some embodiments, the process for preparing the amorphous form of ibrutinib includes:
(a) dissolving ibrutinib in dimethyl sulfoxide to achieve a homogeneous solution; and
(b) contacting the homogeneous solution from step (a) with water to obtain amorphous ibrutinib.

In some embodiments, the process for preparing an amorphous form of ibrutinib also includes:
(c) filtering the amorphous ibrutinib from step (b) to obtain filtered amorphous ibrutinib.

In some embodiments, the process for preparing an amorphous form of ibrutinib can further include:
(d) washing the filtered amorphous ibrutinib from step (c) with an acetone/water mixture to form a wet cake; and
(e) purging the wet cake with an inert gas and drying under reduced pressure to produce said amorphous form of ibrutinib.

In some embodiments, the process for preparing the amorphous form of ibrutinib includes:
(1) combining (S)-3-hydroxypiperidine hydrochloride with trifluoroacetic anhydride to form compound 11

(2) contacting compound 11 with compound 9 to form a reaction mixture;
(3) subjecting the reaction mixture to Mitsunobu reaction conditions to obtain compounds 12 and 12a (4) deprotecting compounds 12 and 12a to form compound 8

(5) combining compound 8 with acryloyl chloride in the presence of inorganic base to form an acylation reaction mixture;
(6) isolating ibrutinib from said acylation reaction mixture to afford isolated ibrutinib, wherein the isolated ibrutinib comprises an ibrutinib/DMSO solution; and
(7) contacting the ibrutinib/DMSO solution with water to obtain amorphous ibrutinib.

For steps not specifically discussed below, reference is made to the preceding paragraphs.

The ibrutinib/DMSO solution formed in step (6), above, may be produced through any of the means described in the above synthesis of ibrutinib. A notable difference from this embodiment and embodiments where solid ibrutinib is isolated from the reaction mixture is the removal of the need to dissolve ibrutinib in DMSO when preparing an amorphous form of ibrutinib. This removes handling steps and improves the efficiency of preparing amorphous ibrutinib.

As noted in the summary of the invention and when describing the process for preparing ibrutinib, a person of skill in the art will appreciate that selected steps in the process may be conducted independent of the origin of starting material or intermediates.

For example, in one embodiment, step (5) can be conducted independent of the process used to prepare compound 8. In this embodiment, amorphous ibrutinib is prepared by (5) combining compound 8 with acryloyl chloride in the presence of inorganic base to form an acylation reaction mixture;
(6) isolating ibrutinib from said acylation reaction mixture to afford isolated ibrutinib, wherein the isolated ibrutinib comprises an ibrutinib/dimethyl sulfoxide (DMSO) solution; and
(7) contacting the ibrutinib/DMSO solution with water to obtain amorphous ibrutinib.

A person of skill in the art will recognize that further embodiments described in the process for preparing ibrutinib are also applicable to the process for preparing amorphous ibrutinib described herein.

In some embodiments, the process for preparing an amorphous form of ibrutinib also includes:
(8) filtering the amorphous ibrutinib from step (7) to obtain filtered amorphous ibrutinib.

In some embodiments, the process for preparing an amorphous form of ibrutinib can further include:
(9) drying the amorphous ibrutinib under reduced pressure to produce said amorphous form of ibrutinib.

It is also understood that steps (d) and (e) as well as step (9) of the previously mentioned processes for preparing amorphous ibrutinib may be used interchangeably between processes.

Figure 2:
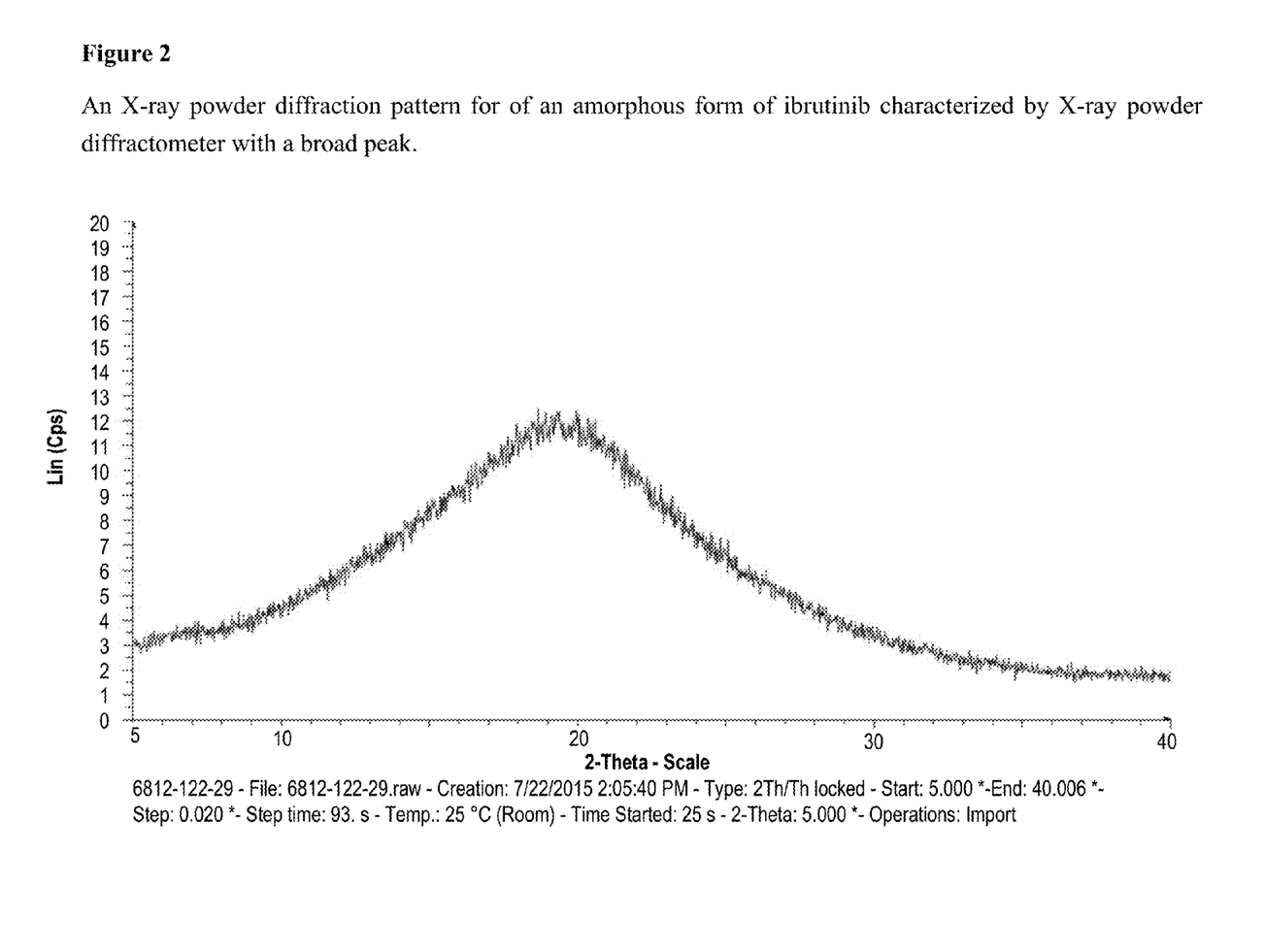
FIG. 2 provides an XRPD pattern for an amorphous form of ibrutinib.

In some embodiments, an amorphous form of ibrutinib prepared by the processes described herein is provided. The amorphous form of ibrutinib described herein is characterized by a powder X-ray diffraction pattern substantially as depicted in FIG. 2.

In some embodiments, the present invention provides a composition including a pharmaceutically acceptable excipient and an amorphous form of ibrutinib prepared by the process described herein.

IV. Examples

The following examples are provided to further illustrate, but not to limit this invention.

Experimental Methodology

X-ray Powder Diffraction patterns were collected on a Bruker AXS D8 Advance diffractometer using Cu Kα1 radiation (40 kV, 40 mA), θ-2θ goniometer, and divergence of V4 and receiving slits, a Ge monochromator and LynxEye detector. The representative XRPD pattern was collected under ambient condition.

The details of the scanning parameters are:
Angular range: 5-40°
Step size: 0.02°
Scan speed: 0.6 sec/step Example 1. Preparation of Compound 11

(S)-3-Hyroxypiperidine hydrochloride (13.7 g, 99.5 mmol) and DCM (68 mL) were added to a suitable reactor equipped with a thermal couple and an overhead stirrer. Et$_3$N (55.5 mL, 397.9 mmol) was added to the mixture at 30° C. The reaction mixture was cooled to 0-10° C. A solution of TFAA (18.01 mL, 129.3 mmol) in DCM (27 mL) was added at 10° C. The resulting solution was warmed to 20-30° C. and stirred at 20-30° C. for over 3 hr. When the reaction was complete as determined by TLC analysis, the reaction was quenched by the addition of 1M HCl (aq) (55 mL). The mixture was stirred at 20-30° C. for 10-20 min, and then the phases were allowed to separate. The aqueous layer was removed. The organic layer was concentrated under reduced pressure at 45° C. The residue was chromatographed on a column of silica gel with n-heptane/EtOAc (4:1) to provide compound 11 (16.6 g, 85%).

$^1$H NMR (400 Hz, MHz, CDCl$_3$) δ 3.91-3.79 (m, 2.5H), 3.59-3.27 (m, 2.5H), 2.02-1.88 (m, 2H), 1.71-1.66 (m, 2H).

Example 2. Preparation of Compound 8

Compound 11 (39.08 g, 198.2 mmol), compound 9 (20.0 g, 65.95 mmol), triphenylphosphine (51.81 g, 198.2 mmol), and THF (500 mL) were added into a four-necked round bottom flask equipped with a mechanical stirrer and a thermometer under nitrogen at 30° C. A solution containing diisopropyl azodicarboxylate (40 mL, 198.2 mmol) in THF (40 mL) was slowly added over 1.5 hr period of whilst maintaining the reaction mixture temperature at 30° C. The solution was stirred for 3 hr at 20-30° C. When the reaction was complete as determined by HPLC analysis, the solution was concentrated under reduced pressure (40-50 torr) at 45° C. to about 120 mL. MeOH (240 mL) was added to the reaction mixture at 30° C. To the crude compound 12 and 12a/MeOH solution, an aqueous solution of 25% NaOH (32 g, 198.2 mmol) was added at 30° C. The solution was stirred for 2 hr at 20-30° C. When the reaction was complete as determined by HPLC analysis, 5M HCl (aq) (66.95 mL) was slowly added while maintaining the temperature at 55° C. The mixture was stirred at 45-55° C. for 3 hr. When the reaction was complete as determined by HPLC analysis, the reaction mixture was concentrated under reduced pressure (10-50 torr) at 45° C. to about 140 mL. Water (280 mL) was added to the reaction mixture, and the solution was concentrated under reduced pressure (10-50 torr) at 55° C. to about 140 mL. Water (240 mL) and EtOAc (400 mL) was added to the reaction mixture at 30° C. The mixture was stirred at 20-30° C. for 10-20 min, and then the phases were allowed to separate and the aqueous layer was saved. 1M HCl (200 mL) was added to the organic layer and stirred at 20-30° C. for 10-20 min. The phases were allowed to separate and the organic layer was removed. The aqueous layers were combined, and EtOAc (200 mL, 10 vol) was added to the combined aqueous layers at 30° C. The mixtures were stirred at 20-30° C. for 10-20 min. The phases were allowed to separate and the organic layer was removed. 25% NaOH was added to the remaining aqueous layer to adjust the pH of the aqueous layer to 8-11 while maintaining the temperature at 20-30° C. After the reaction mixtures stirred for 3 hr at 20-30° C., the solid was filtered and the wet cake was washed with water (23 mL). The wet cake was dried below 50° C. under vacuum and nitrogen to afford compound 8 (21.6 g, 84.8%).

$^1$H NMR (400 Hz, MHz, DMSO) δ 8.24 (s, 1H), 7.68-7.64 (m, 2H), 7.47-7.41 (m, 2H), 7.21-7.11 (m, 5H), 4.71-4.65 (m, 1H), 3.09-3.06 (m, 1H), 2.97-2.90 (m, 1H), 2.50-2.45 (m, 1H), 2.16-2.01 (m, 2H), 1.77-1.74 (m, 1H), 1.61-1.52 (m, 1H),

Example 3. Preparation of Ibrutinib

H$_2$O (28 mL, 5 vol), compound 8 (5.58 g, 14.45 mmol, 1.0 equiv), K$_2$CO$_3$ (2.20 g, 15.9 mmol, 1.1 equiv), and DCM (75 mL, 15 vol) were added to a reactor equipped with a thermocouple and an overhead stirrer at 20-30° C. Butylated hydroxytoluene (BHT) (32 mg, 0.14 mmol, 0.01 equiv) was added to the reaction mixture at 20-30° C. A solution containing distilled acryloyl chloride (1.17 mL, 14.45 mmol, 1.0 equiv) in DCM (11.16 mL, 2 vol) was slowly added over a 0.5 hr period to the reaction mixture while maintaining the temperature at 30° C. The solution was stirred for 0.5 hr at 20-30° C. When the reaction was complete as determined by HPLC analysis, the phases were allowed to separate and the aqueous layer was removed. The organic layer was concentrated under reduced pressure at 45° C. The residue was chromatographed on a column of silica gel with MeOH/DCM (3:97) to provide ibrutinib (7.29 g, 91%).

$^1$H NMR (400 Hz, MHz, MeOH) δ 8.24 (s, 1H), 8.27 (s, 1H), 7.68 (d, J=8.4 Hz, 4H), 7.42 (m, 4H), 7.19 (m, 2H), 7.15 (d, J=8.4 Hz, 4H), 7.10 (m, 2H), 6.67 (dd, J=16.6, 10.6 Hz, 1H), 6.83 (dd, J=16.6, 10.6 Hz, 1H), 6.22 (d, J=16.8 Hz, 1H), 6.15 (d, J=16.8 Hz, 1H), 5.78 (d, J=10.4 Hz, 1H), 5.64 (d, J=10.4 Hz, 1H), 4.86 (m, 2H), 4.65 (d, J=12.4 Hz, 1H), 4.22 (m, 1H), 3.88 (dd, J=13.0, 9.4 Hz, 1H), 3.51 (m, 1H), 4.28 (m, 1H), 4.12 (m, 1H), 3.33 (m, 1H), 3.22 (t, J=10.4 Hz, 1H), 2.23 (m, 2H), 2.38 (m, 2H), 2.08 (m, 2H), 1.72 (m, 2H)

Example 4. Preparation of Amorphous Form of Ibrutinib 2 g of ibrutinib was added to 16 mL of DMSO at about 23° C. The resulting mixture was stirred till complete dissolution. The completely dissolved mixture was slowly added to 100 mL water at about 23° C. with stirring at 200 rpm. Stirring continued for about 0.5 hour. The resulting suspension was filtered and the solid was reslurried with about 50 mL of 5% acetone/water (v/v=5/95) for about 0.3 hr to obtain a wet cake. The wet cake was purged with nitrogen for about 0.5 hr, and then dried at 40° C. under vacuum (100 torr) for 16 hours to provide about 1.25 g of amorphous Ibrutinib.

FIG. 2 shows an X-ray power diffraction pattern for an amorphous form of ibrutinib collected using the experimental methodology described above.

Example 5. Preparation of Compound 11

(S)-3-Hyroxypiperidine hydrochloride (13.7 g, 99.5 mmol) and DCM (68 mL) were added to a suitable reactor equipped with a thermal couple and an overhead stirrer. Et$_3$N (55.5 mL, 397.9 mmol) was added to the mixture at 30° C. The reaction mixture was cooled to 0-10° C. A solution of TFAA (18.01 mL, 129.3 mmol) in DCM (27 mL) was added at 10° C. The resulting solution was warmed to 20-30° C. and stirred at 20-30° C. for over 3 hr. When the reaction was complete as determined by TLC analysis, the reaction was quenched by the addition of 1M HCl (aq) (55 mL). The mixture was stirred at 20-30° C. for 10-20 min, and then the phases were allowed to separate. The aqueous layer was removed. The organic layer was concentrated under reduced pressure at 45° C. The residue was chromatographed on a column of silica gel with EtOAc to provide compound 11 in EtOAc.

$^1$H NMR (400 Hz, MHz, CDCl$_3$) δ 3.91-3.79 (m, 2.5H), 3.59-3.27 (m, 2.5H), 2.02-1.88 (m, 2H), 1.71-1.66 (m, 2H).

Example 6. Preparation of Compound 8

Compound 11 (39.08 g, 198.2 mmol) in EtOAc, compound 9 (20.0 g, 65.95 mmol), triphenylphosphine (51.81 g, 198.2 mmol), and THF (500 mL) were added into a four-necked round bottom flask equipped with a mechanical stirrer and a thermometer under nitrogen at 30° C. A solution containing diisopropyl azodicarboxylate (40 mL, 198.2 mmol) in THF (40 mL) was slowly added over 1.5 hr period of whilst maintaining the reaction mixture temperature at 30° C. The solution was stirred for 3 hr at 20-30° C. When the reaction was complete as determined by HPLC analysis, the solution was concentrated under reduced pressure (40-50 torr) at 45° C. to about 120 mL. MeOH (240 mL) was added to the reaction mixture at 30° C. To the crude compound 12 and 12a/MeOH solution, an aqueous solution of 25% NaOH (32 g, 198.2 mmol) was added at 30° C. The solution was stirred for 2 hr at 20-30° C. When the reaction was complete as determined by HPLC analysis, 5M HCl (aq) (66.95 mL) was slowly added while maintaining the temperature at 55° C. The mixture was stirred at 45-55° C. for 3 hr. When the reaction was complete as determined by HPLC analysis, the reaction mixture was concentrated under reduced pressure (10-50 torr) at 45° C. to about 140 mL. Water (280 mL) was added to the reaction mixture, and the solution was concentrated under reduced pressure (10-50 torr) at 55° C. to about 140 mL. Water (240 mL) and EtOAc (400 mL) was added to the reaction mixture at 30° C. The mixture was stirred at 20-30° C. for 10-20 min, and then the phases were allowed to separate and the aqueous layer was saved. 1M HCl (200 mL) was added to the organic layer and stirred at 20-30° C. for 10-20 min. The phases were allowed to separate and the organic layer was removed. The aqueous layers were combined, and EtOAc (200 mL, 10 vol) was added to the combined aqueous layers at 30° C. The mixtures were stirred at 20-30° C. for 10-20 min. The phases were allowed to separate and the organic layer was removed. 25% NaOH was added to the remaining aqueous layer to adjust the pH of the aqueous layer to 8-11 while maintaining the temperature at 20-30° C. After the reaction mixtures stirred for 3 hr at 20-30° C., the solid was filtered and the wet cake was washed with water (23 mL). The wet cake was dried below 60° C. under vacuum and nitrogen to afford compound 8 (21.6 g, 84.8%).

$^1$H NMR (400 Hz, MHz, DMSO) δ 8.24 (s, 1H), 7.68-7.64 (m, 2H), 7.47-7.41 (m, 2H), 7.21-7.11 (m, 5H), 4.71-4.65 (m, 1H), 3.09-3.06 (m, 1H), 2.97-2.90 (m, 1H), 2.50-2.45 (m, 1H), 2.16-2.01 (m, 2H), 1.77-1.74 (m, 1H), 1.61-1.52 (m, 1H)

Example 7. Preparation of Ibrutinib

H$_2$O (28 mL, 5 vol), compound 8 (5.58 g, 14.45 mmol, 1.0 equiv), K$_2$CO$_3$ (2.20 g, 15.9 mmol, 1.1 equiv), and DCM (75 mL, 15 vol) were added to a reactor equipped with a thermocouple and an overhead stirrer at 20-30° C. Butylated hydroxytoluene (BHT) (32 mg, 0.14 mmol, 0.01 equiv) was added to the reaction mixture at 20-30° C. A solution containing distilled acryloyl chloride (1.17 mL, 14.45 mmol, 1.0 equiv) in DCM (11.16 mL, 2 vol) was slowly added over a 0.5 hr period to the reaction mixture while maintaining the temperature at 30° C. The solution was stirred for 0.5 hr at 20-30° C. When the reaction was complete as determined by HPLC analysis, the phases were allowed to separate and the aqueous layer was removed. The organic layer was concentrated under reduced pressure at 45° C. The residue was chromatographed on a column of silica gel with EtOAc/Acetone. The fractions containing ibrutinib are combined and concentrated at 40° C. under reduced pressure. DMSO (1 vol) was added at 40° C. Concentrated at 40° C. under reduced pressure till no distillate was observed. DMSO (7 vol) was added to afford ibrutinib/DMSO solution.

$^1$H NMR (400 Hz, MHz, MeOH) δ 8.24 (s, 1H), 8.27 (s, 1H), 7.68 (d, J=8.4 Hz, 4H), 7.42 (m, 4H), 7.19 (m, 2H), 7.15 (d, J=8.4 Hz, 4H), 7.10 (m, 2H), 6.67 (dd, J=16.6, 10.6 Hz, 1H), 6.83 (dd, J=16.6, 10.6 Hz, 1H), 6.22 (d, J=16.8 Hz, 1H), 6.15 (d, J=16.8 Hz, 1H), 5.78 (d, J=10.4 Hz, 1H), 5.64 (d, J=10.4 Hz, 1H), 4.86 (m, 2H), 4.65 (d, J=12.4 Hz, 1H), 4.22 (m, 1H), 3.88 (dd, J=13.0, 9.4 Hz, 1H), 3.51 (m, 1H), 4.28 (m, 1H), 4.12 (m, 1H), 3.33 (m, 1H), 3.22 (t, J=10.4 Hz, 1H), 2.23 (m, 2H), 2.38 (m, 2H), 2.08 (m, 2H), 1.72 (m, 2H)

Example 8. Preparation of Amorphous Form of Ibrutinib

The previously prepared mixture containing ibrutinib in DMSO was slowly added to water at about 23° C./200-300 rpm, and followed by stirring for about 0.5 hour. The resulting suspension was filtered and the wet cake was dried at 40° C. under vacuum to provide the amorphous form of ibrutinib.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:
1. A process for the preparation of ibrutinib, comprising:
(5) combining compound 8 with acryloyl chloride in the presence of inorganic base to form an acylation reaction mixture; and
(6) isolating ibrutinib from said acylation reaction mixture to afford isolated ibrutinib.

2. The process of claim 1, wherein the inorganic base is selected from the group consisting of Li$_2$CO$_3$, K$_2$CO$_3$, Cs$_2$CO$_3$, Na$_2$CO$_3$, NaHCO$_3$, KHCO$_3$, and combinations thereof.

3. The process of claim 1, wherein step (5) is conducted in an aqueous solvent mixture comprising one or more organic solvents.

4. The process of claim 3, wherein the aqueous solvent mixture is a biphasic reaction system comprising an aqueous phase and an organic phase.

5. The process of claim 3, wherein the one or more organic solvents are selected from the group consisting of dichloromethane, ethyl acetate, 2-methyltetrahydrofuran, isopropyl acetate, and combinations thereof.

6. The process of claim 5, wherein the one or more organic solvents is dichloromethane.

7. The process of claim 4, wherein ibrutinib is isolated in step (6) by removal of the aqueous phase without washing steps.

8. The process of claim 7, wherein the isolated ibrutinib comprises an ibrutinib/organic solvent solution.

9. The process of claim 8, wherein the organic solvent in the isolated ibrutinib/organic solvent solution is DMSO.

10. The process of claim 7, wherein step (6) further comprises concentrating the organic phase.

11. The process of claim 10, wherein the isolated ibrutinib comprises solid ibrutinib.

12. The process of claim 1, wherein step (5) is conducted at a temperature below 40° C.

13. The process of claim 12, wherein step (5) is conducted at a temperature of about 20-30° C.

14. The process of claim 1, wherein compound 8 is prepared by (2) contacting compound 11

11 with compound 9

9 to form a reaction mixture;

(3) subjecting the reaction mixture to Mitsunobu reaction conditions to obtain compounds 12 and 12a

12

12a and (4) deprotecting compounds 12 and 12a to form compound 8.

15. The process of claim 14, wherein the Mitsunobu reaction conditions of step (3) comprise an inert atmosphere, triphenylphosphine, a solvent, and diisopropyl azodicarboxylate.

16. The process of claim 15, wherein the solvent is selected from the group consisting of tetrahydrofuran, 2-methyltetrahydrofuran, dimethylformamide, dichloromethane, and combinations thereof.

17. The process of claim 16, wherein the solvent is tetrahydrofuran.

18. The process of claim 14, wherein step (3) is conducted at a temperature of about 20-30° C.

19. The process of claim 15, wherein step (4) comprises
(i) combining compounds 12 and 12a with NaOH and MeOH to form a basic deprotection reaction mixture; and
(ii) adding a sufficient amount of HCl to the basic deprotection reaction mixture to form an acidic deprotection reaction mixture with a pH of about −1 to about 5.

20. The process of claim 14, wherein compound 11

11 is prepared by
(1) combining (S)-3-hydroxypiperidine hydrochloride with trifluoroacetic anhydride to form compound 11.

21. A process for preparing ibrutinib, said process comprising:
(1) combining (S)-3-hydroxypiperidine hydrochloride with trifluoroacetic anhydride to form compound 11

(2) contacting compound 11 with compound 9 to form a reaction mixture;
(3) subjecting the reaction mixture to Mitsunobu reaction conditions to obtain compounds 12 and 12a (4) deprotecting compounds 12 and 12a to form compound 8

(5) combining compound 8 with acryloyl chloride in the presence of inorganic base to form an acylation reaction mixture; and
(6) isolating ibrutinib from said acylation reaction mixture to afford isolated ibrutinib.

22. The process of claim 21, wherein the isolated ibrutinib comprises solid ibrutinib.

23. The process of claim 21, further comprising:
(7) dissolving the isolated ibrutinib from step (6) in dimethyl sulfoxide to achieve a homogeneous solution; and
(8) contacting the homogeneous solution from step (7) with water to obtain amorphous ibrutinib.

24. The process of claim 23, further comprising:
(9) filtering the amorphous ibrutinib from step (8) to obtain filtered amorphous ibrutinib.

25. The process of claim 24, further comprising:
(10) washing the filtered amorphous ibrutinib from step (9) with an acetone/water mixture to form a wet cake; and
(11) purging the wet cake with an inert gas and drying under reduced pressure to produce said amorphous form of ibrutinib.

26. The process of claim 25, wherein the inert gas is nitrogen.

27. The process of claim 1,
wherein the isolated ibrutinib from step (6) comprises an ibrutinib/dimethyl sulfoxide (DMSO) solution, said process further comprising
(7) contacting the ibrutinib/DMSO solution with water obtain amorphous ibrutinib.

28. The process of claim 27, further comprising:
(8) filtering the amorphous ibrutinib from step (7) to obtain filtered amorphous ibrutinib.

29. The process of claim 28, further comprising:
(9) drying the amorphous ibrutinib under reduced pressure to produce said amorphous form of ibrutinib.

30. A composition comprising a pharmaceutically acceptable excipient and an amorphous form of ibrutinib prepared by the process of claim 23.

* * * * *